US012622777B2

(12) United States Patent
Wu et al.

(10) Patent No.: US 12,622,777 B2
(45) Date of Patent: May 12, 2026

(54) HAPTIC MANAGEMENT FOR SURGICAL IMPLANTS

(71) Applicant: Alcon Inc., Fribourg (CH)

(72) Inventors: Yinghui Wu, Cedar Hill, TX (US);
Harlen Hoang, Fort Worth, TX (US);
Nerea Garcia Ramila, Arlington, TX (US)

( * ) Notice: Subject to any disclaimer, the term of this patent is extended or adjusted under 35 U.S.C. 154(b) by 835 days.

(21) Appl. No.: 17/819,990

(22) Filed: Aug. 16, 2022

(65) Prior Publication Data

US 2023/0097833 A1     Mar. 30, 2023

Related U.S. Application Data

(60) Provisional application No. 63/250,467, filed on Sep. 30, 2021.

(51) Int. Cl.
A61F 2/16          (2006.01)

(52) U.S. Cl.
CPC ............ A61F 2/1678 (2013.01); A61F 2/167 (2013.01); A61F 2002/1683 (2013.01)

(58) Field of Classification Search
CPC . A61F 2/1678; A61F 2/167; A61F 2002/1683
See application file for complete search history.

(56) References Cited

U.S. PATENT DOCUMENTS 7,156,854 B2     1/2007   Brown et al.
8,308,736 B2     11/2012  Boukhny et al.

| | | |
|---|---|---|
| 8,308,799 B2 | 11/2012 | Chen et al. |
| 8,377,076 B2 | 2/2013 | Downer et al. |
| 8,956,408 B2 | 2/2015 | Smiley et al. |
| 8,968,396 B2 | 3/2015 | Matthews et al. |
| 9,480,555 B2 | 11/2016 | Downer et al. |
| 9,610,155 B2 | 4/2017 | Matthews et al. |
| 9,693,858 B2 | 7/2017 | Hildebrand et al. |
| 9,855,139 B2 | 1/2018 | Matthews et al. |
| 10,172,706 B2 | 1/2019 | Auld et al. |
| 10,195,020 B2 | 2/2019 | Matthews et al. |
| 10,568,735 B2 | 2/2020 | Brown et al. |
| 10,588,780 B2 | 3/2020 | Van Noy et al. |
| 11,039,953 B2 | 6/2021 | Balachandran |
| 12,004,944 B2 | 6/2024 | Weston |
| 2008/0097460 A1 | 4/2008 | Boukhny et al. |

(Continued)

FOREIGN PATENT DOCUMENTS

| EP | 1800623 A1 | 6/2007 |
|---|---|---|
| EP | 1857076 B1 | 7/2010 |

(Continued)

*Primary Examiner* — Ashley L Fishback
*Assistant Examiner* — Chima U Igboko
(74) *Attorney, Agent, or Firm* — Darin Deaver

(57)          ABSTRACT

An apparatus that can be used to fold an intraocular lens or other implant before inserting it into an eye in various locations using variable surgical techniques. Some embodiments may comprise or consist essentially of a haptic folding mechanism configured to fold one or more haptics onto the top of an optic prior to the optic being folded into a nozzle. In some embodiments, a leading haptic lifter or lifting mechanism can be configured to raise and constrain a leading haptic during implant delivery. This leading haptic folding mechanism can actively lift the leading haptic onto the top of the optic.

18 Claims, 15 Drawing Sheets

(56)                References Cited

U.S. PATENT DOCUMENTS

| | | |
|---|---|---|
| 2008/0147081 A1 | 6/2008 | Pynson |
| 2008/0221584 A1 | 9/2008 | Downer |
| 2010/0057093 A1 | 3/2010 | Ide et al. |
| 2011/0265779 A1 | 11/2011 | Vandrak et al. |
| 2012/0022548 A1 | 1/2012 | Zacharias |
| 2013/0197532 A1 | 8/2013 | Boukhny et al. |
| 2013/0253527 A1 | 9/2013 | Schneider et al. |
| 2014/0012277 A1 | 1/2014 | Matthews et al. |
| 2014/0257315 A1 | 9/2014 | Wu |
| 2014/0276898 A1 | 9/2014 | Novak et al. |
| 2015/0238687 A1 | 8/2015 | Novakovic et al. |
| 2015/0282928 A1 | 10/2015 | Auld et al. |
| 2016/0087460 A1 | 3/2016 | Rich et al. |
| 2017/0007237 A1 | 1/2017 | Yates et al. |
| 2017/0027686 A1 | 2/2017 | Nagasaka et al. |
| 2017/0119522 A1 | 5/2017 | Auld et al. |
| 2018/0049866 A1 | 2/2018 | Fayyaz et al. |
| 2018/0200046 A1 | 7/2018 | Brown |
| 2018/0200047 A1* | 7/2018 | Wu ........................ A61F 2/1678 |
| 2020/0179101 A1 | 6/2020 | Flowers et al. |
| 2020/0179102 A1 | 6/2020 | Chen et al. |
| 2020/0179103 A1 | 6/2020 | Auld et al. |
| 2020/0188089 A1* | 6/2020 | Auld ........................ A61F 2/167 |
| 2020/0197169 A1 | 6/2020 | Wu |
| 2020/0197170 A1 | 6/2020 | Auld et al. |
| 2021/0052371 A1 | 2/2021 | Singh et al. |
| 2022/0265420 A1 | 8/2022 | Kelp |

FOREIGN PATENT DOCUMENTS

| | | |
|---|---|---|
| EP | 3560457 A1 | 10/2019 |
| JP | 2010063777 B | 10/2013 |
| JP | 2016503716 A | 2/2016 |
| WO | 2014145562 A1 | 9/2014 |
| WO | 2020065516 A1 | 4/2020 |
| WO | 2020128762 A1 | 6/2020 |
| WO | 2020151908 A1 | 7/2020 |

* cited by examiner

HAPTIC MANAGEMENT FOR SURGICAL IMPLANTS

PRIORITY CLAIM

This application claims the benefit of priority of U.S. Provisional Patent Application Ser. No. 63/250,467 titled "HAPTIC MANAGEMENT FOR SURGICAL IMPLANTS," filed on Sep. 30, 2021, whose inventors are Yinghui Wu, Harlen Hoang and Nerea Garcia Ramila, which is hereby incorporated by reference in its entirety as though fully and completely set forth herein.

TECHNICAL FIELD

The invention set forth in the appended claims relates generally to eye surgery, including, without limitation, systems, apparatuses, and methods for inserting an implant into an eye.

BACKGROUND

The human eye can suffer from a variety of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may be used to fold and compress an intraocular lens or other optical implant before inserting it into the eye in various locations using variable surgical techniques. Such embodiments may comprise or consist essentially of a haptic folding mechanism configured to fold one or more haptics onto the top of an optic prior to the optic being folded into a nozzle.

In some embodiments, a leading haptic lifter or lifting mechanism can be configured to raise and constrain a leading haptic during implant delivery. This leading haptic folding mechanism can actively lift the leading haptic and allow it to fall onto the top of the optic.

More generally, some embodiments of an apparatus for eye surgery may comprise an implant bay, an implant disposed in the implant bay, and a haptic lifter. The implant may comprise an optic body, a leading haptic, and a trailing haptic, and the haptic lifter may comprise a lifter arm and a lever arm. The lever arm may be configured to rotate the lifter arm in the implant bay from a first position to a second position. The lifter arm may be configured to engage the leading haptic between the first position and the second position to lift the leading haptic relative to the optic body. In more particular embodiments, the lifter arm may be configured to retain the implant in the implant bay in the first position. Some embodiments of the apparatus may additionally comprise a plunger configured to advance the optic body under the leading haptic with the lifter arm in the second position.

In other embodiments, an apparatus may comprise a nozzle and an implant bay coupled to the nozzle. The implant bay may comprise a base, a cap coupled to the base to form a cavity within the implant bay, and a retention clip. An implant, such as an intraocular lens, may be disposed between the base and the cap. The implant may comprise an optic body, a leading haptic, and a trailing haptic. The apparatus may further comprise a haptic lifter having a lifter arm, a lever arm, and a pin between the lifter arm and the lever arm. The haptic lifter may be disposed through the cap so that the lifter arm is at least partially disposed between the base and the cap, and the lever arm is at least partially exposed external to the implant bay. The retention clip may engage the pin so that the haptic lifter is rotatable about the pin to move the lifter arm from a first position to a second position, and the lifter arm can be configured to engage the leading haptic between the first position and the second position to lift the leading haptic relative to the optic body. An actuator may be coupled to the base and may be configured to advance the implant from the implant bay into the nozzle if the lifter arm is in the second position.

In other embodiments, an apparatus for managing an intraocular lens or other implant may comprise a base and a cap coupled to the base to form a cavity for holding the intraocular lens between the base and the cap. The apparatus may further comprise a pin and a retention clip configured to rotatably couple the pin to the cap. A lifter arm may be coupled to the pin and at least partially disposed in the cavity between the base and the cap, and a lever arm may be coupled to the pin and at least partially exposed above the cap. The lever arm may be configured to move the pin to rotate the lifter arm from a first position to a second position, and the lifter arm may be configured to engage a leading haptic of the intraocular lens as the lifter arm moves from the first position to the second position, which can lift the leading haptic relative to an optic body of the intraocular lens.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
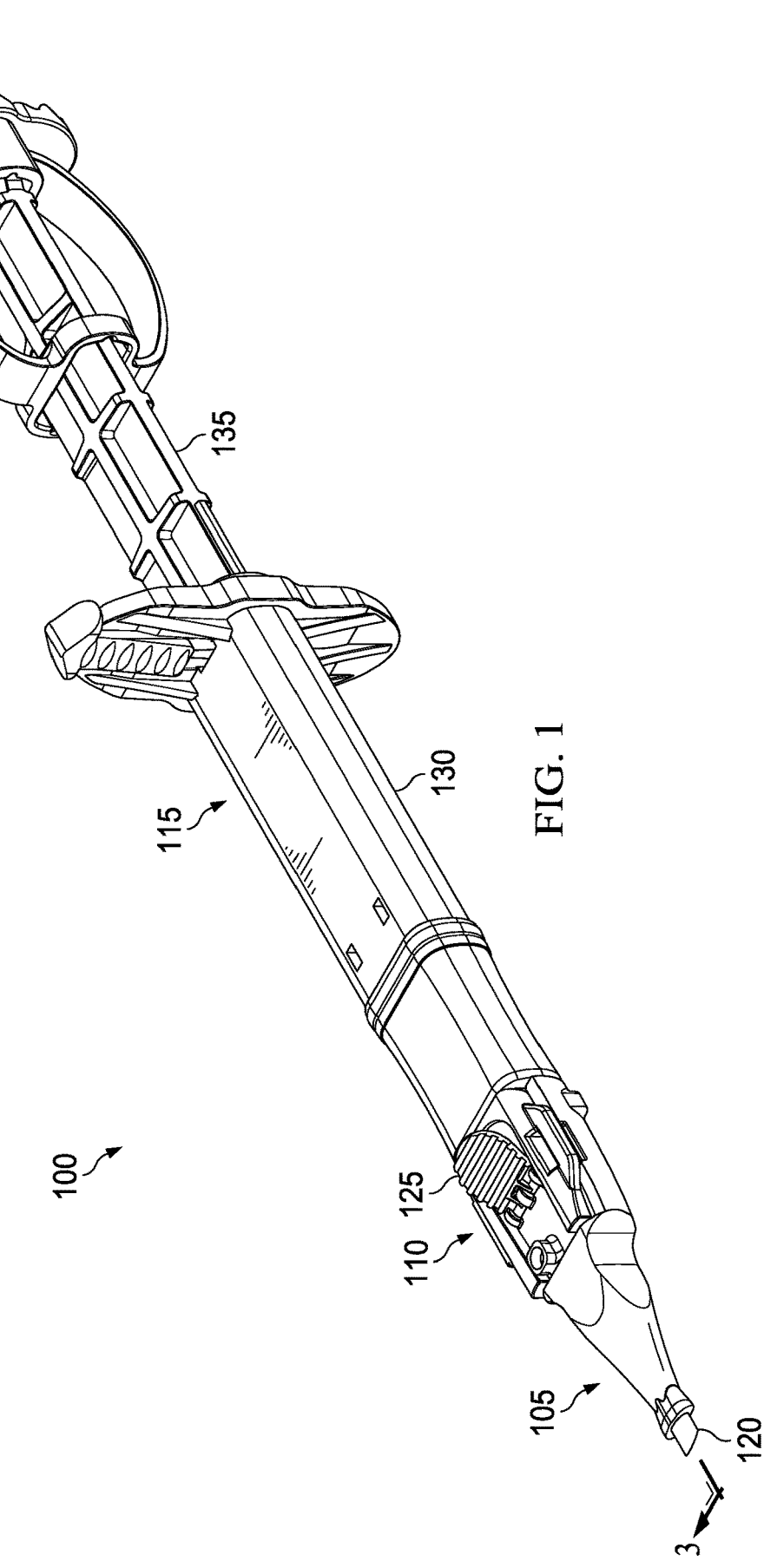
FIG. 1 is an isometric view of an example apparatus for delivering an implant into an eye.

FIG. 1 is an isometric view of an example of an apparatus 100 that can deliver an implant into an eye. In some embodiments, the apparatus 100 may comprise two or more modules, which can be configured to be coupled and decoupled as appropriate for storage, assembly, use, and disposal. As illustrated in FIG. 1, some embodiments of the apparatus 100 may include a nozzle 105, an implant bay 110 coupled to the nozzle 105, and an actuator 115 coupled to the implant bay 110.

The nozzle 105 generally comprises a tip 120 adapted for insertion through an incision into an eye. The size of the tip 120 may be adapted to surgical requirements and techniques as needed. For example, small incisions are generally preferable to reduce or minimize healing times. Incisions of less than 3 millimeters may be preferable in some instances, and the tip 120 of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may comprise a haptic lifter 125, which can be configured to lift or fold one or more features, such as haptics, of an intraocular lens.

The actuator 115 is generally configured to advance an implant from the implant bay 110 into the nozzle 105, and thereafter from the nozzle 105 through an incision and into an eye. In the example of FIG. 1, the actuator 115 comprises a housing 130 and a plunger 135.

In general, components of the apparatus 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, implant bay 110 may be mechanically coupled to the actuator 115 and may be mechanically and fluidly coupled to the nozzle 105. In some embodiments, components may also be coupled by virtue of physical proximity, being integral to a single structure, or being formed from the same piece of material.

Figure 2:
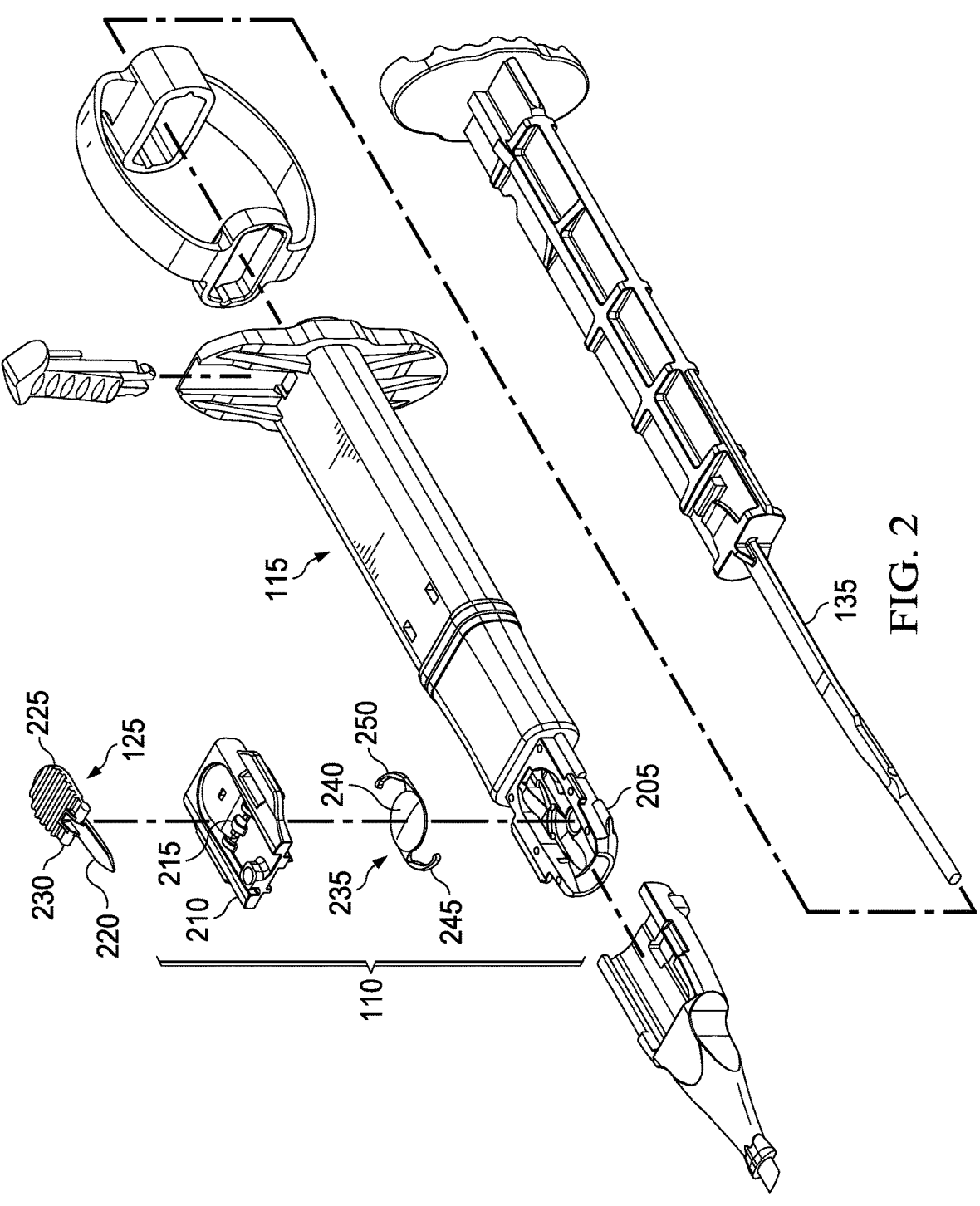
FIG. 2 is an exploded view of the example apparatus of FIG. 1.

FIG. 2 is an exploded view of the apparatus 100 of FIG. 1, illustrating additional details that may be associated with some embodiments. For example, the implant bay 110 of FIG. 2 comprises a base 205 and a cap 210, which may be coupled to the base 205. The base 205 may extend from or be coupled to actuator 115 in some examples. As shown in FIG. 2, some embodiments of the cap 210 may comprise one or more retention clips 215. Some embodiments of the haptic lifter 125 may comprise a lifter arm 220 and a lever arm 225, as illustrated in FIG. 2. The lever arm 225 may be coupled to the lifter arm 220. In the example of FIG. 2, the haptic lifter 125 further comprises a pin 230 between the lifter arm 220 and the lever arm 225. The lifter arm 220 may be inserted through an aperture (not visible in FIG. 2) in the cap 210 so that the retention clips 215 can engage the pin 230.

An implant 235 may be disposed between the base 205 and the cap 210. In the example of FIG. 2, the implant 235 is an intraocular lens having an optic body 240. In some examples, the optic body 240 may have a shape similar to that of a natural lens of an eye. Examples of suitable materials may include silicone, acrylic, and combinations of such suitable materials. The implant 235 may also comprise one or more features for positioning the optic body 240 within an eye, such as a leading haptic 245 and a trailing haptic 250. In the example of FIG. 2, the leading haptic 245 and the tailing haptic 250 extend from opposing sides of the optic body 240. In some instances, the implant 235 may be filled with a fluid, such as a fluid-filled accommodating intraocular lens.

Figure 3:
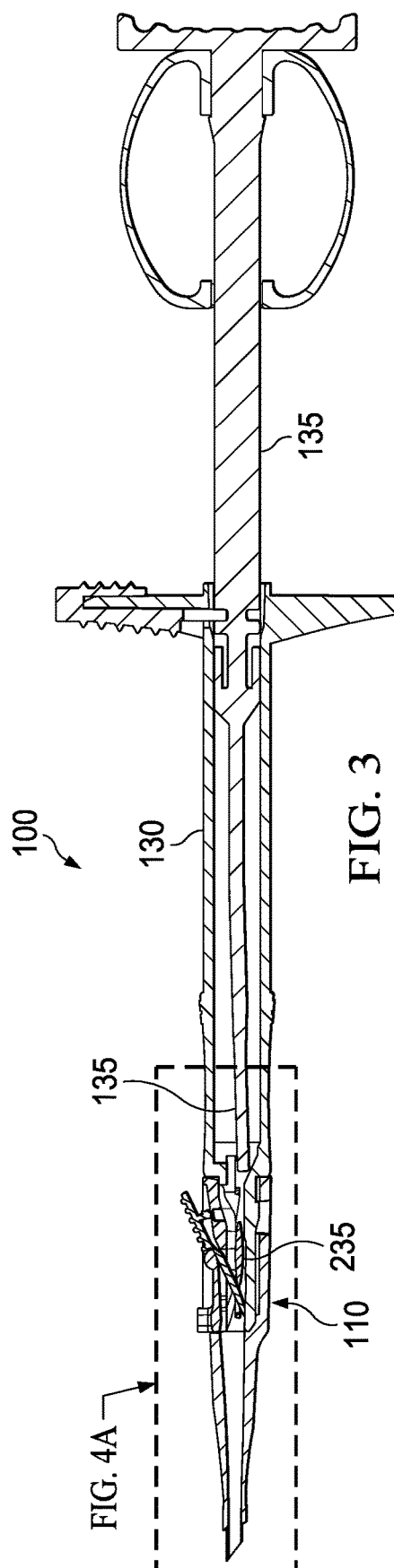
FIG. 3 is a section view of the example apparatus of FIG. 1.

FIG. 3 is a section view of the apparatus 100 of FIG. 1, taken along line 3-3, illustrating additional details that may be associated with some embodiments. As illustrated in the example of FIG. 3, the implant 235 may be initially stored in the implant bay 110 in some embodiments. At least a portion of the plunger 135 may be disposed within the housing 130. In some embodiments, at least a portion of the plunger 135 may extend into the implant bay 110. In some embodiments, a distal end of the plunger 135 may be configured to engage the implant 235 in the implant bay 110.

Figure 4A:
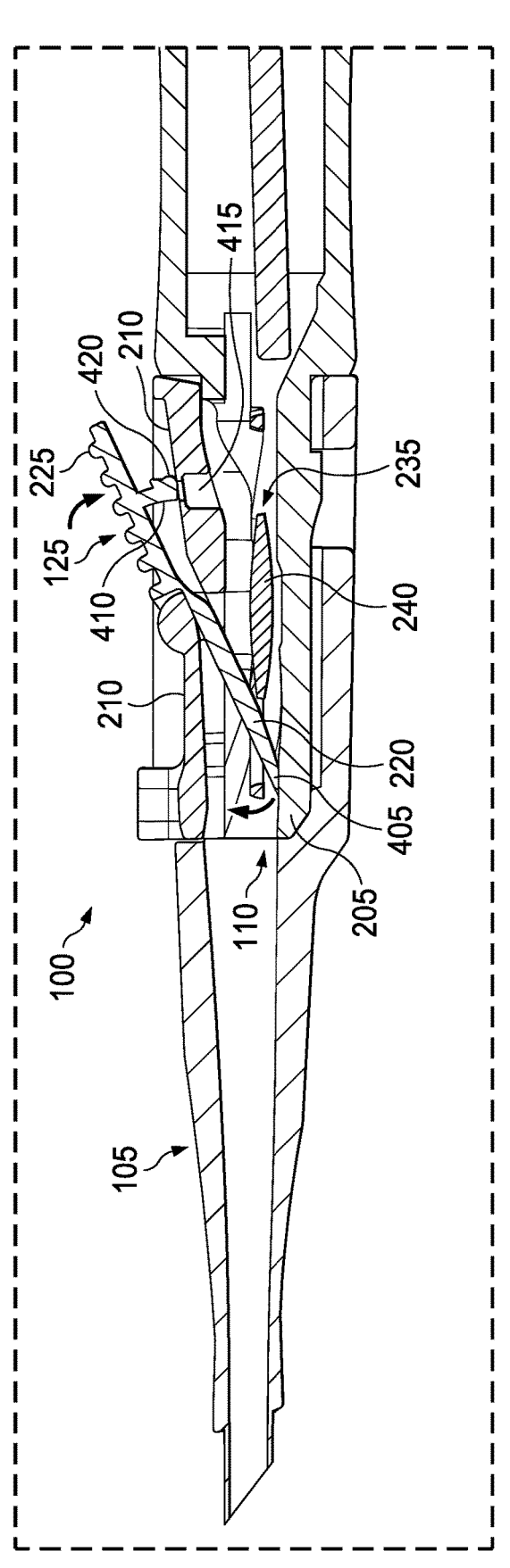
FIG. 4A is a detail view of a portion of the apparatus of FIG. 3.

FIG. 4A is a detail view of a portion of the apparatus 100 of FIG. 3, illustrating additional details that may be associated with some embodiments. For example, the cap 210 may be coupled to the base 205, forming a cavity in the implant bay 110 between the cap 210 and the base 205. The haptic lifter 125 of FIG. 4A is disposed through the cap 210, so that the lifter arm 220 is at least partially disposed in the cavity between the base 205 and the cap 210, within the implant bay 110, and the lever arm 225 is at least partially exposed outside the implant bay 110. In some examples, a first position of the lifter arm 220 may be configured to retain the implant 235 within the implant bay 110. In more specific examples, the lifter arm 220 may be configured to limit or prevent movement of the implant 235 from the implant bay 110 into the nozzle 105 in the first position. In FIG. 4A, for example, the lifter arm 220 is illustrated in a first position, wherein a distal end 405 is in contact with the base 205 between the optic body 240 and the nozzle 105 to allow the lifter arm 220 to retain the implant 235 in the implant bay 110.

In some embodiments, the haptic lifter 125 may additionally comprise a detent mechanism configured to hold the lifter arm 220 in the first position. For example, the haptic lifter 125 of FIG. 4A comprises a detent arm 410 coupled to the lever arm 225. The detent arm 410 in the example of FIG. 4A is configured to engage cap 210. More specifically, the detent arm 410 of FIG. 4A is configured to be inserted into an aperture 415 in the cap 210. The detent arm 410 may have at least a first detent 420, which can be configured to prevent rotation of the haptic lifter 125 if the lifter arm 220 is in the first position. For example, the first detent 420 may rest against the aperture 415 to bias the lifter arm 220 against the base 205, or the first detent 420 may be inserted into the aperture 415 to constrain rotation.

Figure 4B:
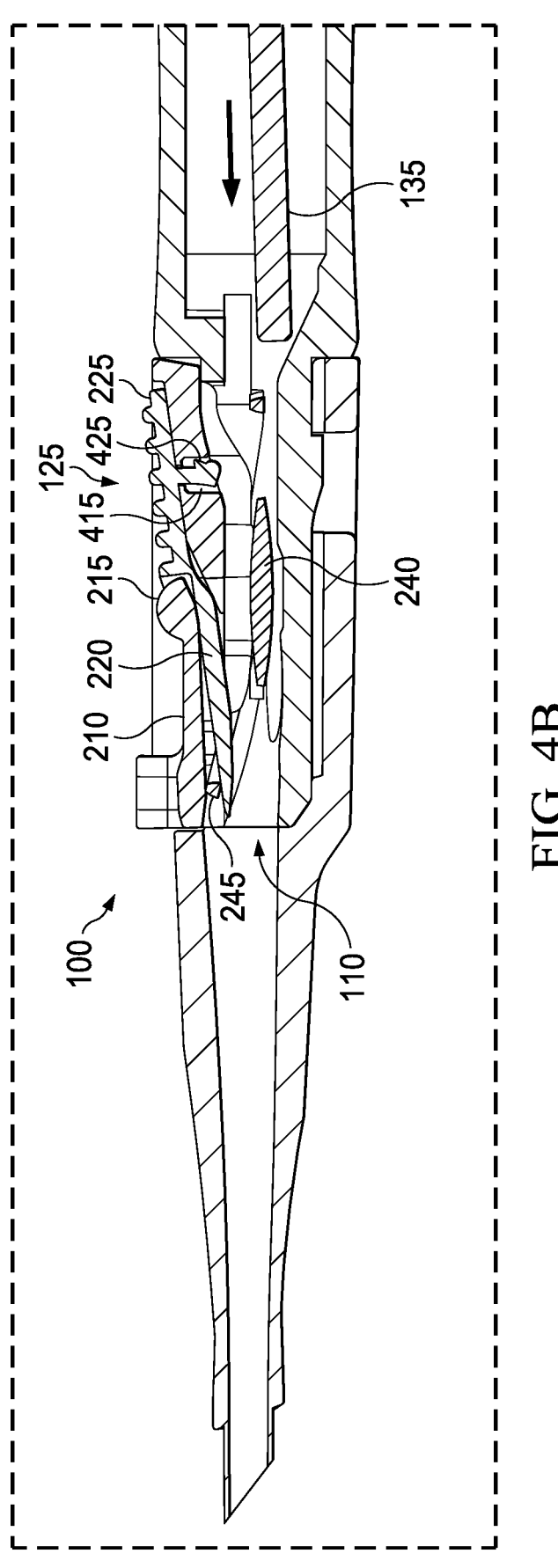
FIG. 4B illustrates additional details that may be associated with the example of FIG. 4A in a second configuration.

FIG. 4B illustrates additional details that may be associated with the example of FIG. 4A in a second configuration. For example, the lever arm 225 may be configured to move the lifter arm 220 in the implant bay 110 from the first position of FIG. 4A to a second position, as illustrated in FIG. 4B. In some embodiments, for example, the haptic lifter 125 may be configured to rotate about the pin 230 (not visible in FIG. 4B) of the haptic lifter 125. In the example of FIG. 4B, the retention clips 215 of the cap 210 can engage the pin 230, substantially constraining movement of the haptic lifter 125 to rotation about the pin 230. Consequently, force applied to the lever arm 225 can rotate the lifter arm 220 about the pin 230 from the first position of FIG. 4A to the second position in FIG. 4B. In some examples, the angle of rotation may be less than ninety (90) degrees. In more particular examples, the angle of rotation may be in a range of about ten (10) degrees to about twenty (20) degrees. An angle of rotation of about sixteen (16) degrees may be advantageous for some embodiments.

As illustrated in the example of FIG. 4B, the lifter arm 220 may be configured to engage the leading haptic 245 as the lifter arm 220 transitions between the first position and the second position. As the lifter arm 220 moves to the second position, the lifter arm 220 can lift a distal portion of the leading haptic 245 relative to the optic body 240, toward the cap 210, as illustrated in the example of FIG. 4B.

In some embodiments, the detent arm 410 may have at least a second detent 425. The second detent 425 may be configured to prevent rotation of the haptic lifter 125 if the lifter arm 220 is in the second position. For example, force applied to the lever arm 225 can move the second detent 425 into the aperture 415 as the lifter arm 220 is rotated to the second position, which can then constrain return rotation.

Figure 4C:
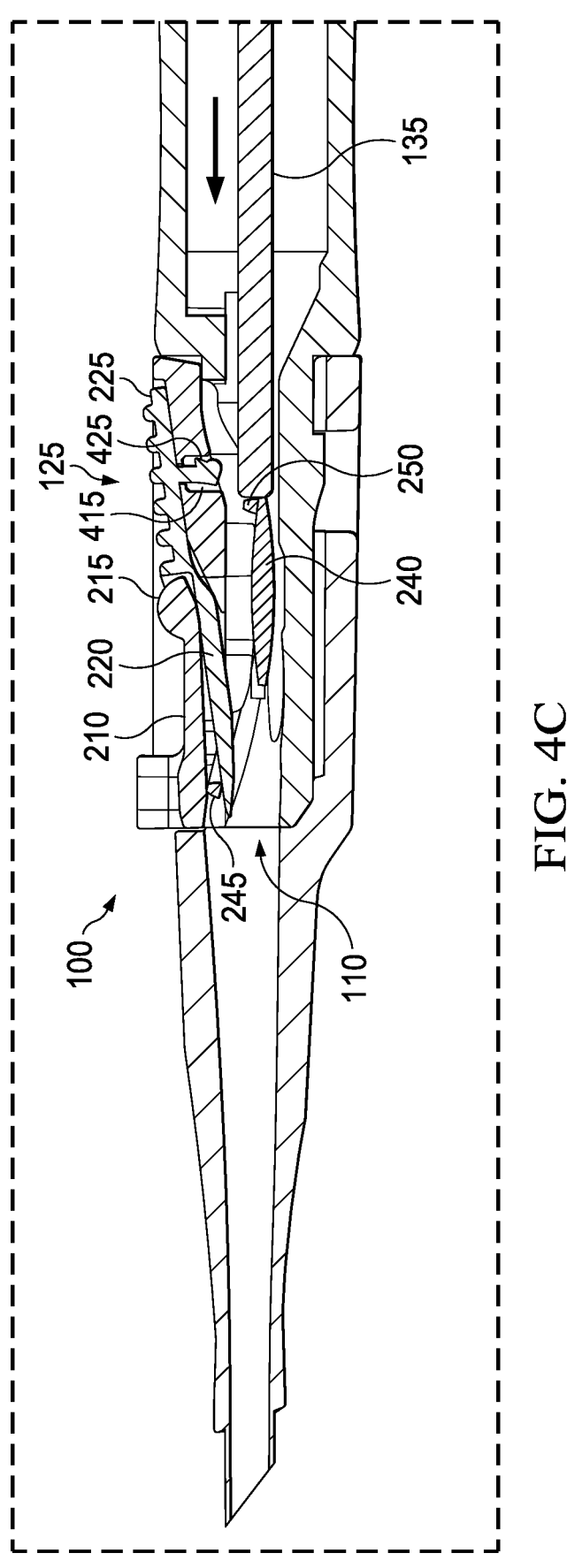
FIG. 4C illustrates additional details that may be associated with the example of FIG. 4A in a third configuration.

FIG. 4C illustrates additional details that may be associated with the example of FIG. 4A in a third configuration. With the lifter arm 220 in the second position, and the leading haptic 245 lifted relative to the optic body 240, the plunger 135 can be advanced toward the implant bay 110 to fold the trailing haptic 250 over the optic body 240, as illustrated in FIG. 4C.

Figure 4D:
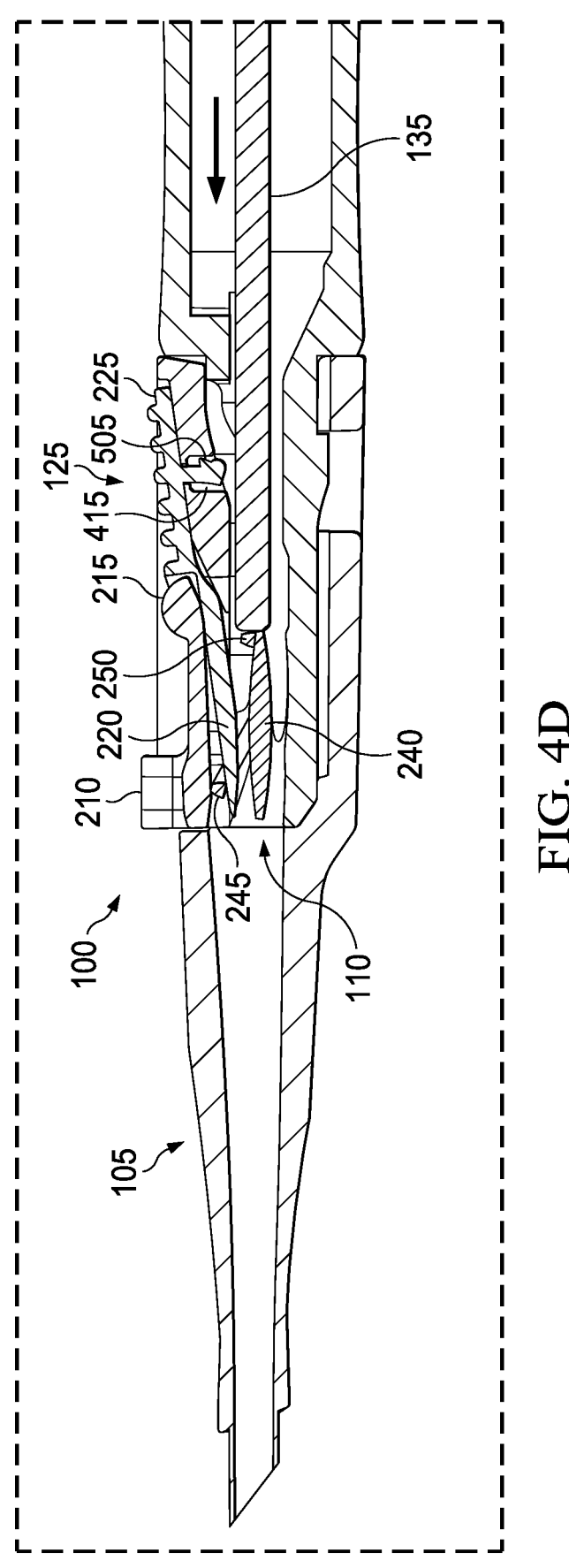
FIG. 4D illustrates additional details that may be associated with the example of FIG. 4A in a fourth configuration.

FIG. 4D illustrates additional details that may be associated with the example of FIG. 4A in a fourth configuration. With the leading haptic 245 lifted and the trailing haptic folded as shown in FIG. 4C, the distal end of the plunger 135 may be advanced through the implant bay 110. Advancement of the plunger 135 can also advance the optic body 240 toward the nozzle 105. In some embodiments, the lifter arm 220 may apply slight pressure against the leading haptic 245 toward the cap 210 in the second position, which can provide resistance to lateral movement of the leading haptic 245 as the optic body 240 is advanced underneath, as illustrated in FIG. 4C. In some embodiments, a haptic constraint may be coupled to the lifter arm 220 or the cap 210 to constrain lateral movement of the leading haptic 245. For example, a haptic constraint may comprise or consist essentially of a groove, notch, protrusion, or catch on or in the lifter arm 220 or the cap 210.

Figure 4E:
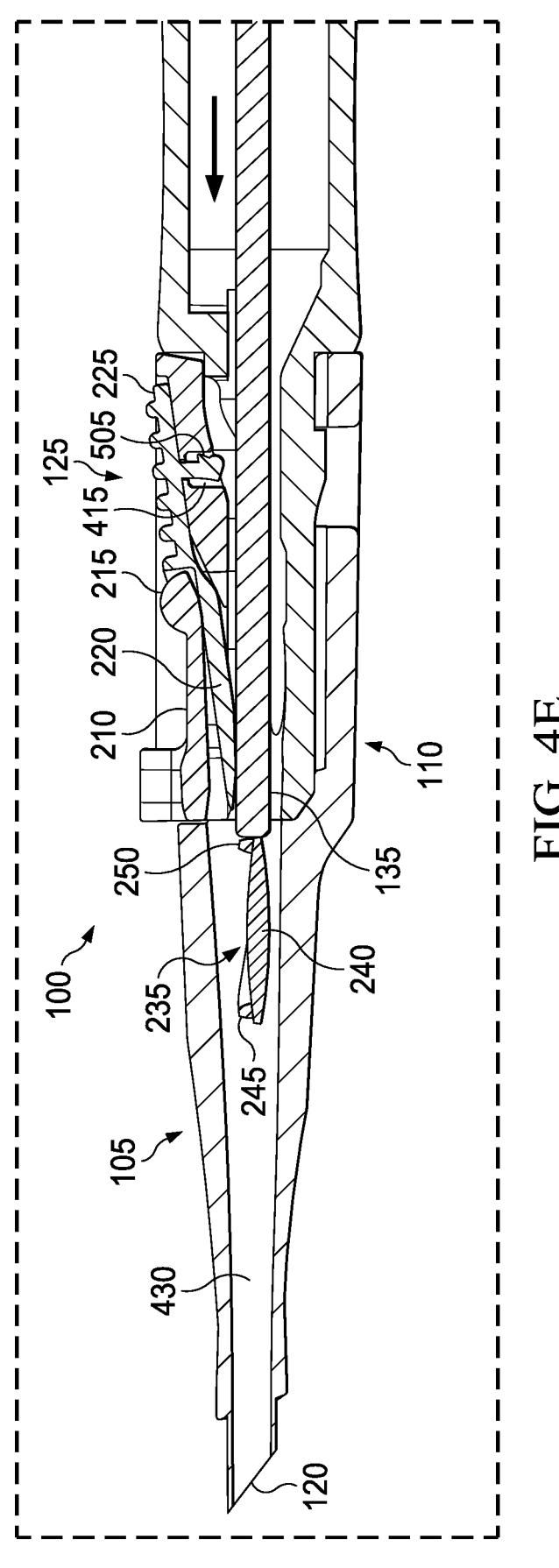
FIG. 4E illustrates additional details that may be associated with the example of FIG. 4A in a fifth configuration.

FIG. 4E illustrates additional details that may be associated with the example of FIG. 4A in a fifth configuration. In the example of FIG. 4E, the optic body 240 can be advanced by the plunger 135 until the leading haptic 245 is released from the lifter arm 220 and falls onto the top of the optic body 240. For example, in some embodiments, advancement of the optic body 240 can create tension in the leading haptic 245 until the distal end of the leading haptic 245 is pulled off the lifter arm 220 onto the optic body 240. The plunger 135 can be advanced further to move the implant 235 in the folded configuration through a delivery lumen 430 in the nozzle 105 until the implant 235 is ejected through the tip 120.

Figure 5:
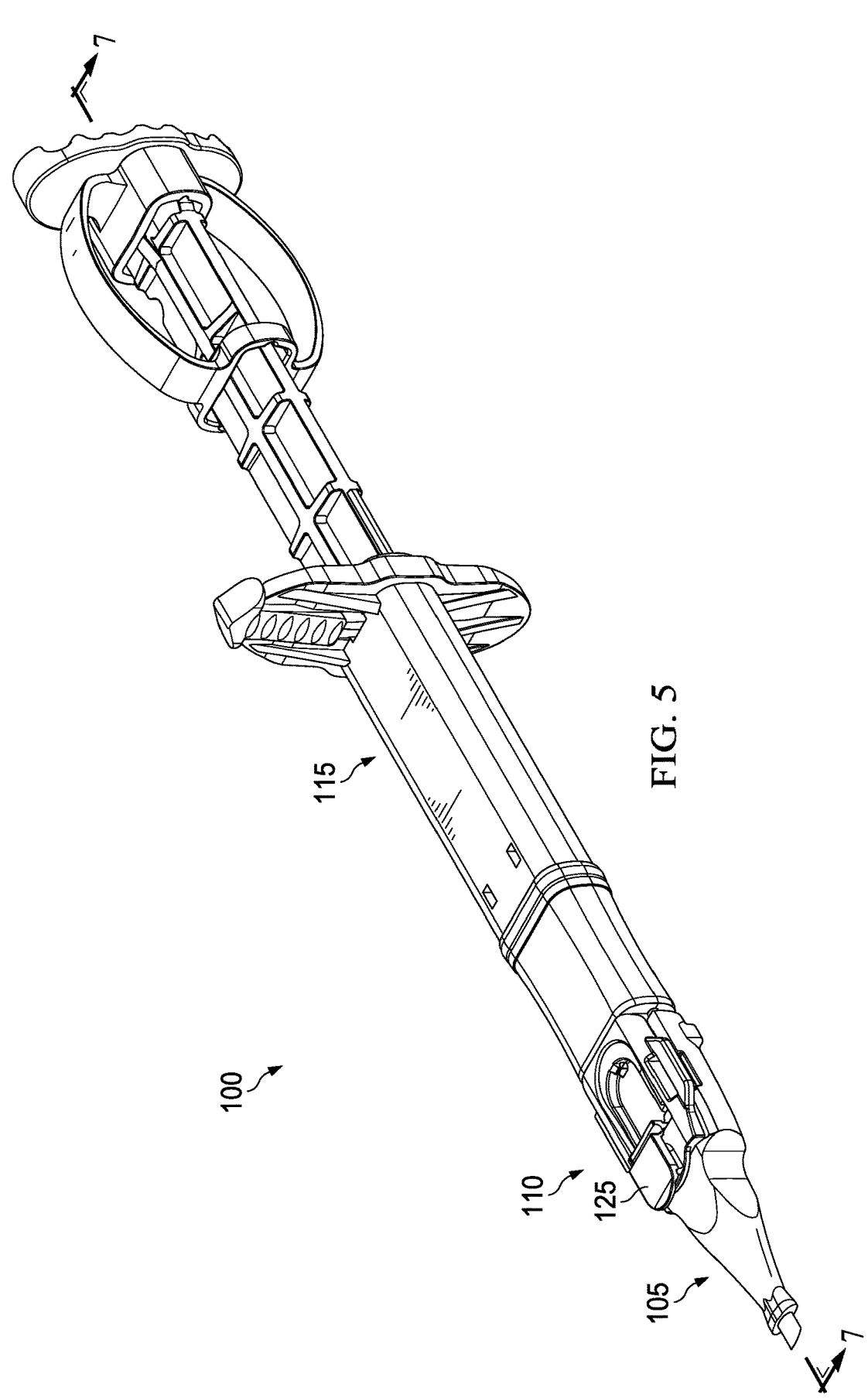
FIG. 5 is an isometric view of another example of an apparatus for delivering an implant into an eye.

FIG. 5 is an isometric view of another example of the apparatus 100. The apparatus 100 of FIG. 5 may include the nozzle 105, the implant bay 110 coupled to the nozzle 105, and the actuator 115 coupled to the implant bay 110. FIG. 5 also illustrates another example of the haptic lifter 125.

Figure 6:
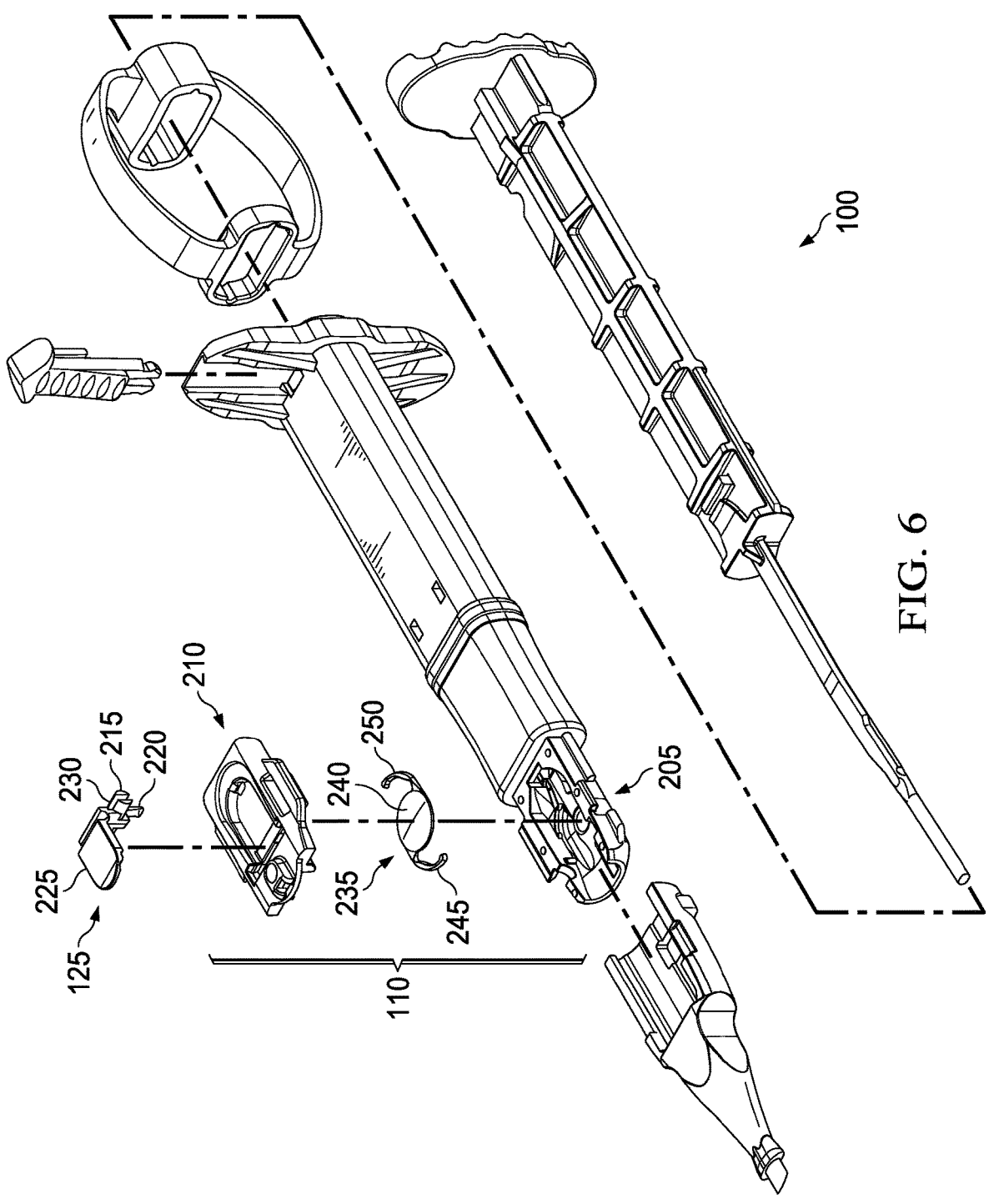
FIG. 6 is an exploded view of the apparatus of FIG. 5.

FIG. 6 is an exploded view of the apparatus 100 of FIG. 5, illustrating additional details that may be associated with some embodiments. For example, the implant bay 110 of FIG. 6 comprises the base 205 and the cap 210. FIG. 6 also illustrates other examples of the retention clips 215, the lifter arm 220, and the lever arm 225. In the example of FIG. 6, the retention clips 215 are coupled to the pin 230, which is coupled to the lifter arm 220 and the lever arm 225. The lifter arm 220 may be inserted through an aperture (not visible in FIG. 6) in the cap 210 so that the retention clips 215 can engage the cap 210.

The implant 235 may be disposed between the base 205 and the cap 210. In the example of FIG. 6, the implant 235 is another example of an intraocular lens having the optic body 240, the leading haptic 245, and the trailing haptic 250. In some instances, the implant 235 may be filled with a fluid, such as a fluid-filled accommodating intraocular lens.

Figure 7:
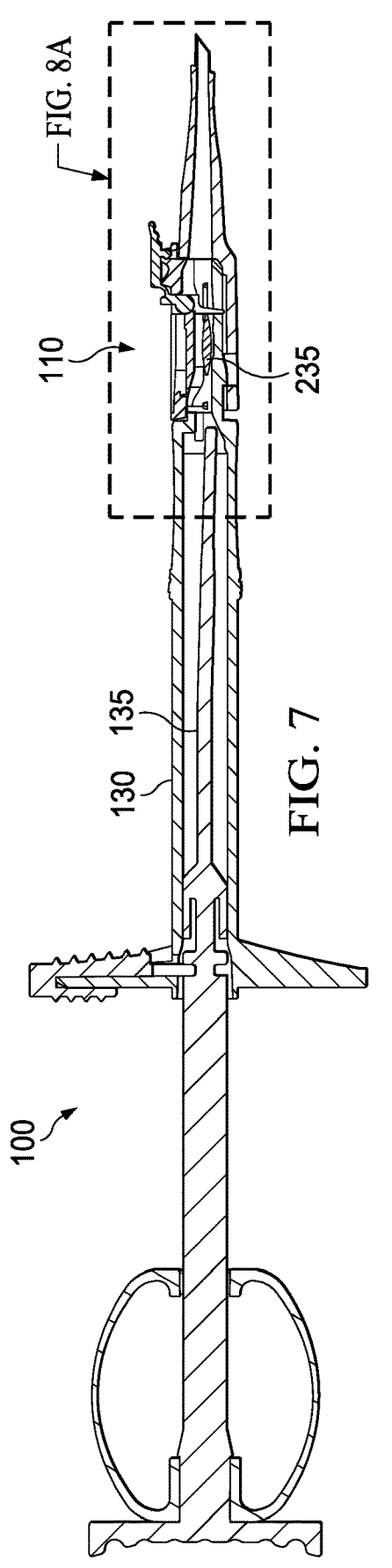
FIG. 7 is a section view of the apparatus of FIG. 5.

FIG. 7 is a section view of the apparatus 100 of FIG. 5, taken along line 7-7, illustrating additional details that may be associated with some embodiments. As illustrated in the example of FIG. 7, the implant 235 may be initially stored in the implant bay 110. At least a portion of the plunger 135 may be disposed within the housing 130. In some embodiments, at least a portion of the plunger 135 may extend into the implant bay 110. In some embodiments, a distal end of the plunger 135 may be configured to engage the implant 235 in the implant bay 110.

Figure 8A:
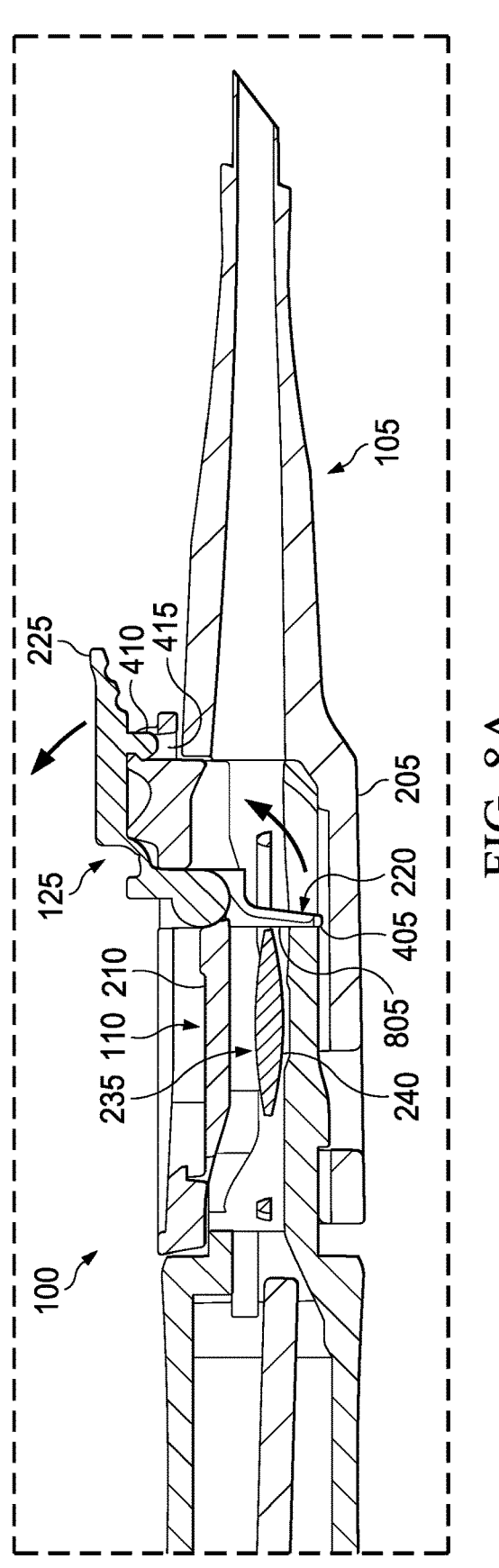
FIG. 8A is a detail view of a portion of the apparatus of FIG. 7.

FIG. 8A is a detail view of a portion of the apparatus 100 of FIG. 7, illustrating additional details that may be associated with some embodiments. For example, the haptic lifter 125 of FIG. 8A is disposed through the cap 210, so that the lifter arm 220 is at least partially disposed between the base 205 and the cap 210, within the implant bay 110, and the lever arm 225 is at least partially exposed outside the implant bay 110. In some examples, a first position of the lifter arm 220 may be configured to retain the implant 235 within the implant bay 110. In more specific examples, the lifter arm 220 may comprise an optic stop 805, which can be configured to limit or prevent movement of the implant 235 from the implant bay 110 into the nozzle 105 if the lifter arm 220 is in the first position. In FIG. 8A, for example, the lifter arm 220 is illustrated in a first position, wherein the distal end 405 is adjacent to or in contact with the base 205 between the optic body 240 and the nozzle 105 to allow the optic stop 805 to retain the implant 235 in the implant bay 110.

The detent arm 410 of FIG. 8A is coupled to the lever arm 225 and is configured to engage cap 210. More specifically, the detent arm 410 of FIG. 8A is configured to be inserted into the aperture 415 in the cap 210 to prevent rotation of the haptic lifter 125 if the lifter arm 220 is in the first position. For example, the detent arm 410 may be inserted into the aperture 415 to constrain rotation.

Figure 8B:
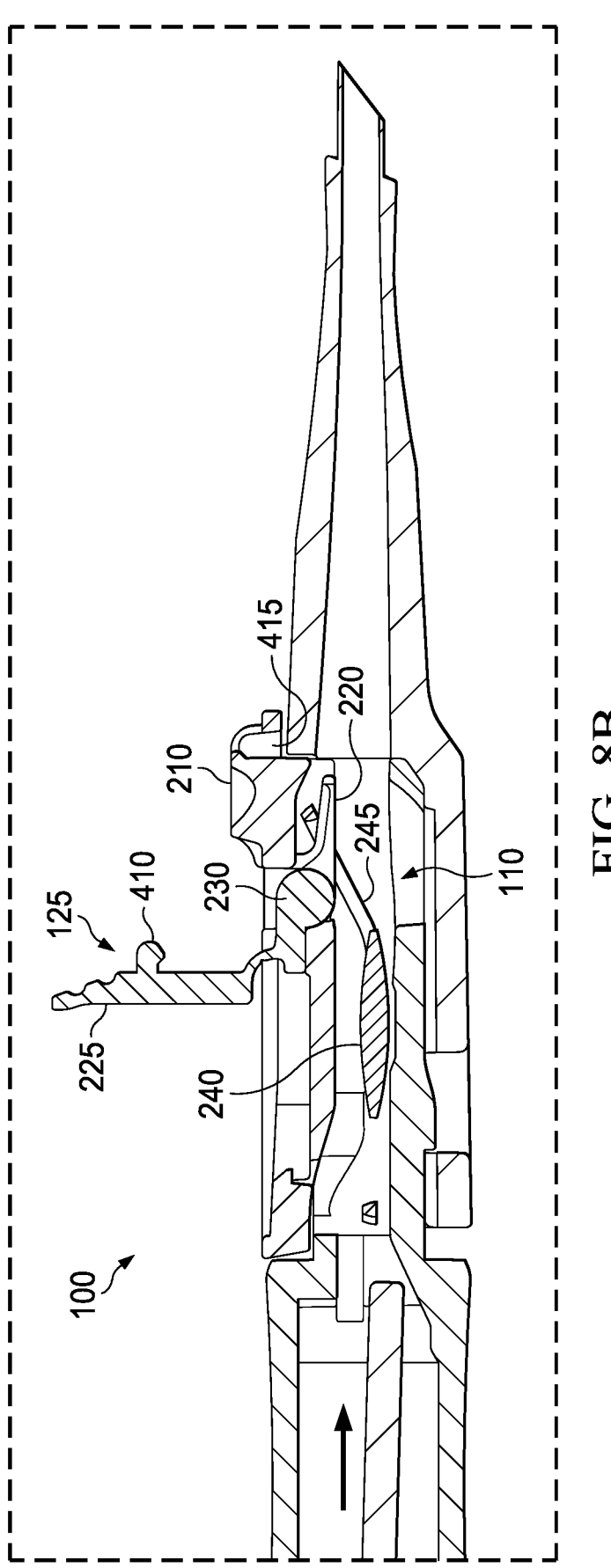
FIG. 8B illustrates additional details that may be associated with the example of FIG. 8A in a second configuration.

FIG. 8B illustrates additional details that may be associated with the example of FIG. 8A in a second configuration. For example, the lever arm 225 may be configured to move the lifter arm 220 in the implant bay 110 from the first position of FIG. 8A to a second position, as illustrated in FIG. 8B. In some embodiments, for example, the haptic lifter 125 may be configured to rotate about the pin 230. In the example of FIG. 8B, the retention clips 215 (not visible in FIG. 8B) can engage the cap 210, substantially constraining movement of the haptic lifter 125 to rotation about the pin 230. Consequently, force applied to the lever arm 225 can release the detent arm 410 from the aperture 415 and rotate the lifter arm 220 about the pin 230 from the first position of FIG. 8A to the second position in FIG. 8B. In some examples, the angle of rotation may be about ninety (90) degrees.

As illustrated in the example of FIG. 8B, the lifter arm 220 may be configured to engage the leading haptic 245 as the lifter arm 220 transitions between the first position and the second position. As the lifter arm 220 moves to the second position, the lifter arm 220 can lift a distal portion of the leading haptic 245 relative to the optic body 240, toward the cap 210, as illustrated in the example of FIG. 8B.

Figure 8C:
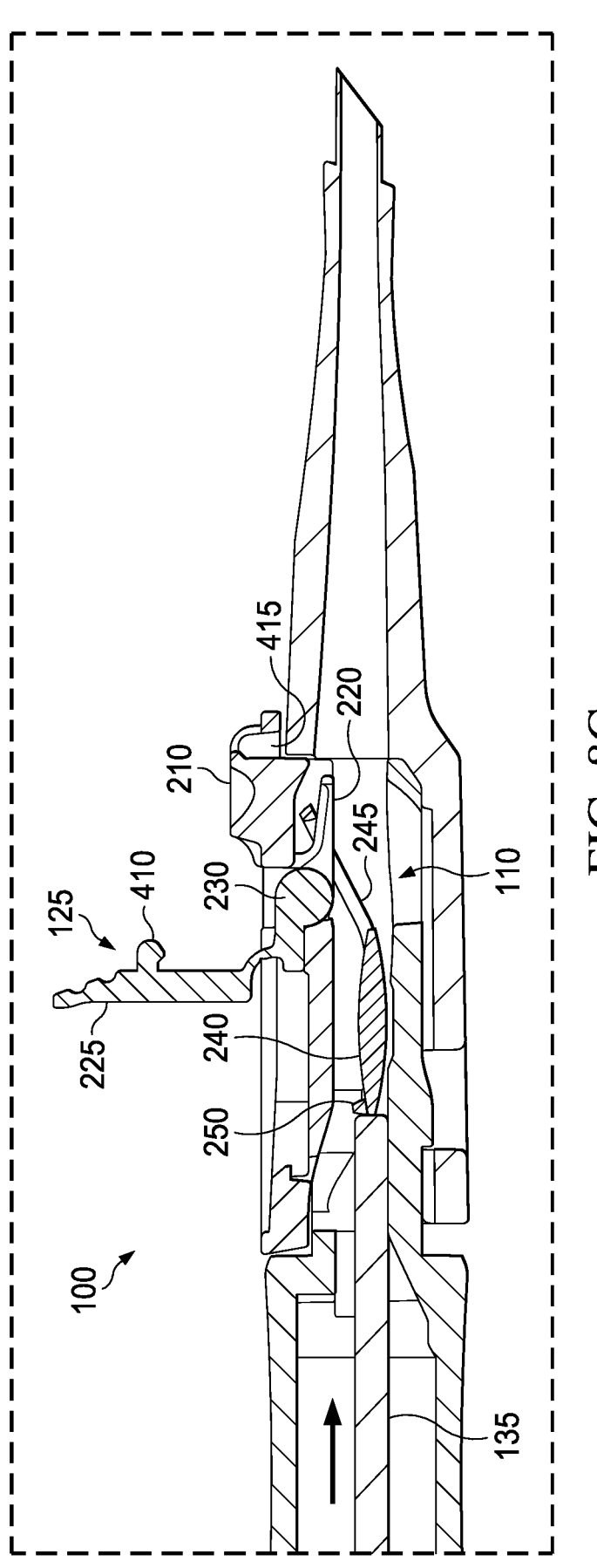
FIG. 8C illustrates additional details that may be associated with the example of FIG. 8A in a third configuration.

FIG. 8C illustrates additional details that may be associated with the example of FIG. 8A in a third configuration. With the lifter arm 220 in the second position, and the leading haptic 245 lifted relative to the optic body 240, the plunger 135 can be advanced toward the implant bay 110 to fold the trailing haptic 250 over the optic body 240, as illustrated in FIG. 8C.

Figure 8D:
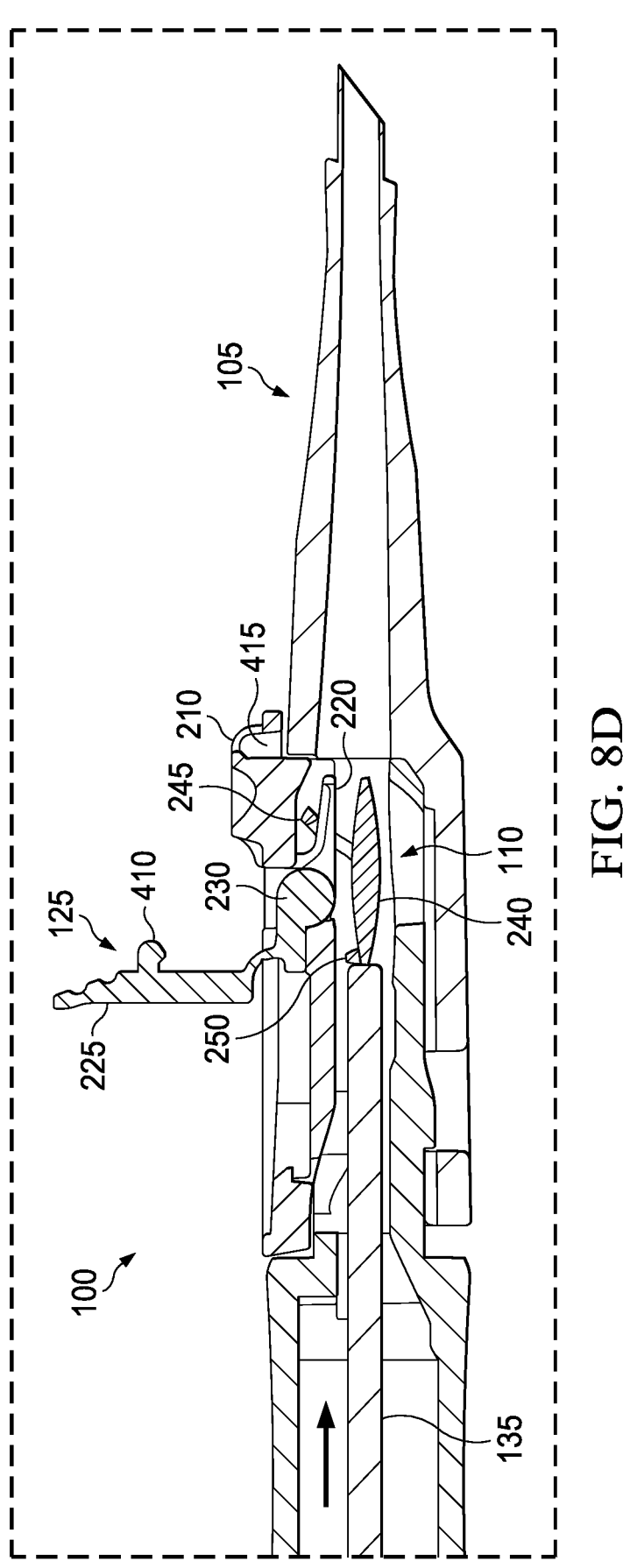
FIG. 8D illustrates additional details that may be associated with the example of FIG. 8A in a fourth configuration.

FIG. 8D illustrates additional details that may be associated with the example of FIG. 8A in a fourth configuration. With the leading haptic 245 lifted and the trailing haptic folded as shown in FIG. 8C, the distal end of the plunger 135 may be advanced through the implant bay 110. Advancement of the plunger 135 can also advance the optic body 240 toward the nozzle 105. In the second position, some embodiments of the lifter arm 220 may apply slight pressure against the leading haptic 245 toward the cap 210, which can provide resistance to lateral movement of the leading haptic 245 as the optic body 240 advances underneath, as illustrated in FIG. 8C. In some embodiments, the lifter arm 220 may have a haptic constraint configured to constrain lateral movement of the leading haptic 245.

Figure 8E:
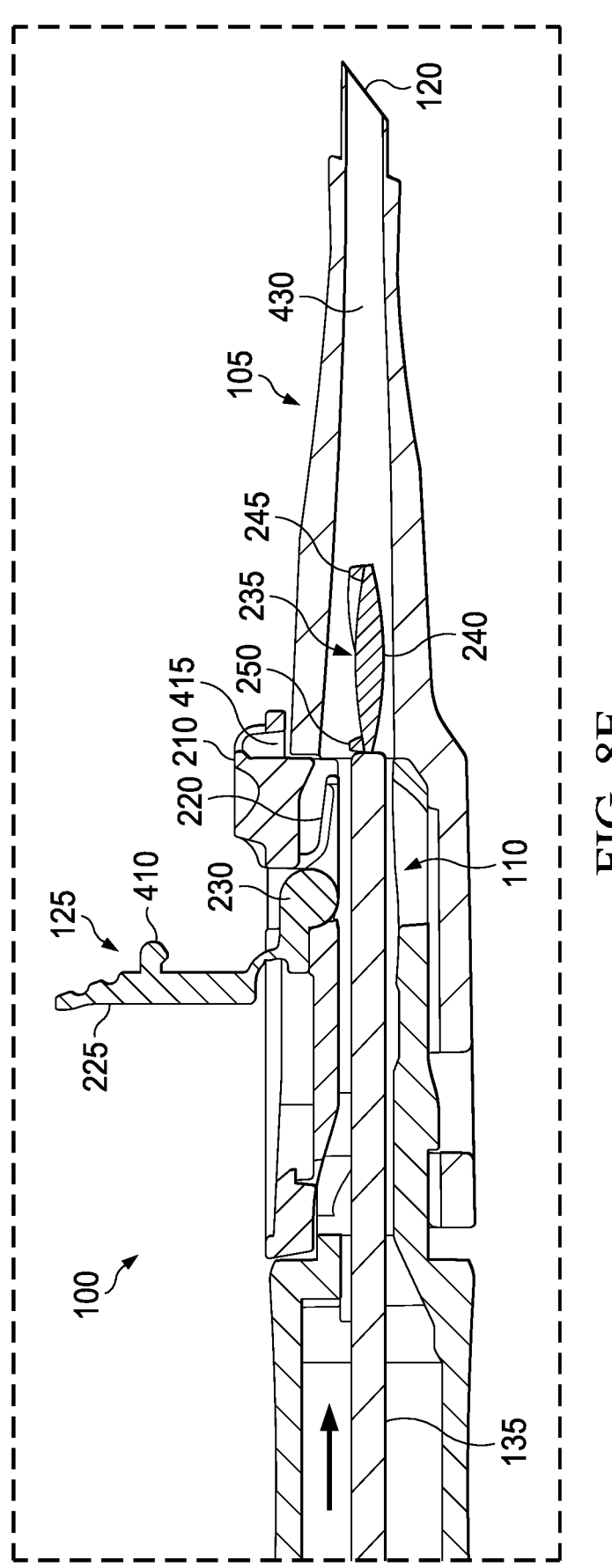
FIG. 8E illustrates additional details that may be associated with the example of FIG. 8A in a fifth configuration.

FIG. 8E illustrates additional details that may be associated with the example of FIG. 8A in a fifth configuration. In the example of FIG. 8E, the optic body 240 can be advanced by the plunger 135 until the leading haptic 245 is released from the lifter arm 220 and falls onto the top of the optic body 240. For example, in some embodiments, advancement of the optic body 240 can create tension in the leading haptic 245 until the distal end of the leading haptic 245 is pulled off the lifter arm 220 onto the optic body 240. The plunger 135 can be advanced further to move the implant 235 in the folded configuration through the delivery lumen 430 in the nozzle 105 until the implant 235 is ejected through the tip 120.

Figures 9A, 9B:
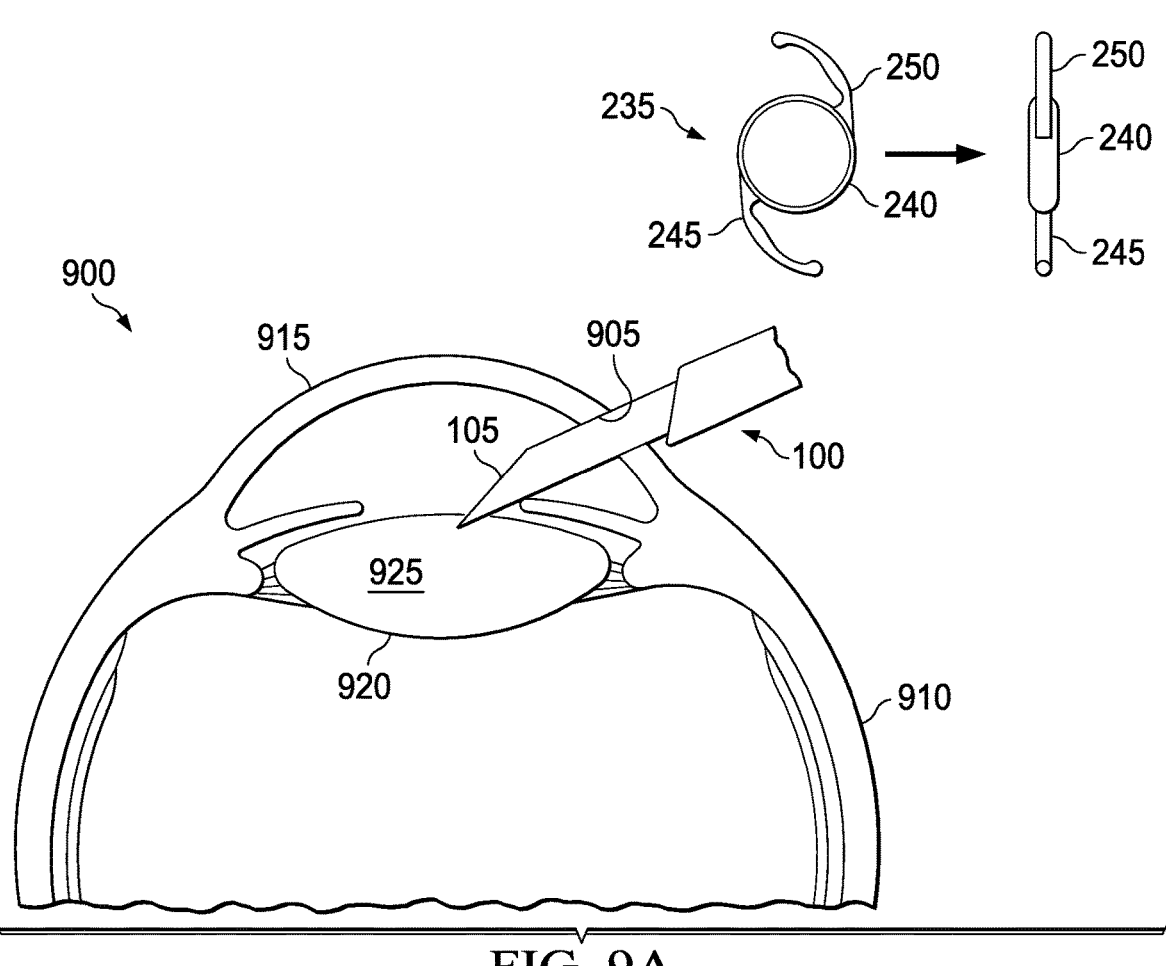
FIGS. 9A-9B are schematic diagrams illustrating an example use of the apparatus to deliver an implant to an eye.

FIGS. 9A-9B are schematic diagrams further illustrating an example use of the apparatus 100 to deliver the implant 235 to an eye 900. As illustrated, an incision 905 may be made in the eye 900 by a surgeon, for example. In some instances, the incision 905 may be made through the sclera 910 of the eye 900. In other instances, an incision may be formed in the cornea 915 of the eye 900. The incision 905 may be sized to permit insertion of a portion of the nozzle 105 to deliver the implant 235 into the capsular bag 920. For example, in some instances, the size of the incision 905 may have a length less than about 3000 microns (3 millimeters). In other instances, the incision 905 may have a length of from about 1000 microns to about 1500 microns, from about 1500 microns to about 2000 microns, from about 2000 microns to about 2500 microns, or from about 2500 microns to about 3000 microns.

After the incision 905 is made, the nozzle 105 can be inserted through the incision 905 into an interior portion 925 of the eye 900. The apparatus 100 can then eject the implant 235 through the nozzle 105 into the capsular bag 920 of the eye 900, substantially as described with reference to FIGS. 4A-4E or FIGS. 8A-8E. In the example of FIG. 9A and FIG. 9B, the implant 235 is illustrative of an intraocular lens having the optic body 240, the leading haptic 245, and a trailing haptic 250. The implant 235 may be delivered in a folded configuration and can revert to a resting state with the leading haptic 245 and the trailing haptic 250 being at least partially curved around the optic body 240, within the capsular bag 920, as shown in FIG. 9B. The capsular bag 920 can retain the implant 235 within the eye 900 in a relationship relative to the eye 900 so that the optic body 240 refracts light directed to the retina (not shown). The leading haptic 245 and the trailing haptic 250 can engage the capsular bag 920 to secure the implant 235 therein. After delivering the implant 235 into the capsular bag 920, the nozzle 105 may be removed from the eye 900 through the incision 905, and the eye 900 can be allowed to heal over a period of time.

The systems, apparatuses, and methods described herein may provide significant advantages. For example, some embodiments may be particularly advantageous for delivering intraocular implants. More particular advantages of some embodiments may include providing high-consistency folding of leading haptics without significantly increasing complexity or cost. Consistent and reliable haptic folding can significantly increase consistency and reliability for implant delivery through small incisions across the diopter range, particularly with a pre-loaded implant delivery system.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may also be combined or eliminated in various configurations for purposes of sale, manufacture, assembly, or use. For example, in some configurations, the nozzle 105, the implant bay 110, and the actuator 115 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for eye surgery, the apparatus comprising:
an implant bay;
an implant disposed in the implant bay, the implant comprising an optic body, a leading haptic, and a trailing haptic;
a haptic lifter comprising a lifter arm and a lever arm coupled to the lifter arm, wherein the lever arm is configured to rotate the lifter arm in the implant bay from a first position to a second position, and the lifter arm is configured to engage the leading haptic between the first position and the second position to lift the leading haptic relative to the optic body; and
a plunger configured to advance the optic body under the leading haptic with the lifter arm in the second position.

2. The apparatus of claim 1, wherein the haptic lifter is configured to retain the implant in the implant bay if the lifter arm is in the first position.

3. The apparatus of claim 1, wherein the lifter arm is configured to retain the implant in the implant bay in the first position.

4. The apparatus of claim 1, wherein the lever arm is configured to rotate the lifter arm about ninety degrees from the first position.

5. The apparatus of claim 1, wherein the lever arm is configured to rotate the lifter arm less than ninety degrees from the first position.

6. The apparatus of claim 5, wherein the lever arm is configured to rotate the lifter arm about ten to twenty degrees from the first position.

7. The apparatus of claim 5, wherein, in the first position, the lifter arm is in contact with a base of the implant bay.

8. The apparatus of claim 1, wherein the lifter arm comprises a distal end having a haptic constraint.

9. The apparatus of claim 1 wherein the lever arm comprises a first detent configured to hold the lifter arm in the first position.

10. The apparatus of claim 1, wherein the lever arm comprises a second detent configured to hold the lifter arm in the second position.

11. The apparatus of claim 1, further comprising the plunger having a distal end configured to fold the trailing haptic over the optic body.

12. The apparatus of claim 1, wherein the plunger is configured to advance the optic body until the leading haptic is released from the lifter arm and falls onto the optic body.

13. An apparatus for eye surgery, the apparatus comprising:
a nozzle;
an implant bay coupled to the nozzle, the implant bay comprising a base, a cap coupled to the base to form a cavity within the implant bay, and a retention clip;
an implant disposed in the cavity, the implant comprising an optic body, a leading haptic, and a trailing haptic;
a haptic lifter comprising a lifter arm, a lever arm, and a pin between the lifter arm and the lever arm, the haptic lifter disposed through the cap so that the lifter arm is at least partially disposed within the cavity, the lever arm is at least partially exposed external to the implant bay, the retention clip engages the pin, the haptic lifter is rotatable about the pin to move the lifter arm from a first position to a second position, and the lifter arm is configured to engage the leading haptic between the first position and the second position to lift the leading haptic relative to the optic body; and
an actuator coupled to the base, the actuator configured to advance the implant from the implant bay into the nozzle with the lifter arm in the second position, wherein the actuator comprises a plunger having a distal end configured to fold the trailing haptic over the optic body.

14. The apparatus of claim 13, wherein the lifter arm is configured to retain the optic body within the implant bay if the lifter arm is in the first position.

15. The apparatus of claim 13, wherein the lifter arm comprises an optic stop configured to retain the optic body within the implant bay if the lifter arm is in the first position.

16. The apparatus of claim 13, wherein the plunger configured to advance the optic body under the leading haptic with the lifter arm in the second position.

17. The apparatus of claim 13, wherein the plunger configured to advance the optic body under the leading haptic with the lifter arm in the second position until the leading haptic is released from the lifter arm and falls onto the optic body.

18. An apparatus for eye surgery, the apparatus comprising:
a nozzle;
an implant bay coupled to the nozzle, the implant bay comprising a base, a cap coupled to the base to form a cavity within the implant bay, and a retention clip;
an implant disposed in the cavity, the implant comprising an optic body, a leading haptic, and a trailing haptic;
a haptic lifter comprising a lifter arm, a lever arm, and a pin between the lifter arm and the lever arm, the haptic lifter disposed through the cap so that the lifter arm is at least partially disposed within the cavity, the lever arm is at least partially exposed external to the implant bay, the retention clip engages the pin, the haptic lifter is rotatable about the pin to move the lifter arm from a first position to a second position, and the lifter arm is configured to engage the leading haptic between the first position and the second position to lift the leading haptic relative to the optic body; and
an actuator coupled to the base, the actuator configured to advance the implant from the implant bay into the nozzle with the lifter arm in the second position, wherein the actuator comprises a plunger configured to advance the optic body under the leading haptic with the lifter arm in the second position.

* * * * *